United States Patent
Jeannin et al.

(10) Patent No.: US 12,288,297 B2
(45) Date of Patent: Apr. 29, 2025

(54) METHOD FOR DISPLAYING A COMFORT-INCREASING AND ESPECIALLY ANTI-MOTION-SICKNESS VISUAL REFERENCE

(71) Applicant: BOARDING RING, Ollioules (FR)

(72) Inventors: Renaud Jeannin, Ollioules (FR); Antoine Jeannin, Ollioules (FR); Hubert Jeannin, Ollioules (FR)

(73) Assignee: BOARDING RING, Ollioules (FR)

( * ) Notice: Subject to any disclaimer, the term of this patent is extended or adjusted under 35 U.S.C. 154(b) by 0 days.

(21) Appl. No.: 18/834,681

(22) PCT Filed: Feb. 1, 2022

(86) PCT No.: PCT/FR2022/050186
§ 371 (c)(1),
(2) Date: Jul. 31, 2024

(87) PCT Pub. No.: WO2023/148434
PCT Pub. Date: Aug. 10, 2023

(65) Prior Publication Data
US 2025/0111612 A1    Apr. 3, 2025

(51) Int. Cl.
*G06T 19/00*    (2011.01)
*G06F 3/01*    (2006.01)

(52) U.S. Cl.
CPC .............. *G06T 19/00* (2013.01); *G06F 3/012* (2013.01)

(58) Field of Classification Search
CPC ................................. G06T 19/00; G06F 3/012
See application file for complete search history.

(56) References Cited

U.S. PATENT DOCUMENTS 7,918,781 B1 * 4/2011 Smyth .................... A61M 21/00
                                                           600/27
12,161,477 B1 * 12/2024 Berme ................. A61B 5/1036
(Continued)

FOREIGN PATENT DOCUMENTS

| EP | 3799027 A1 | 3/2021 |
| WO | 2020141269 A1 | 7/2020 |

OTHER PUBLICATIONS

International Search Report (PCT/ISA/210) with English translation and Written Opinion (PCT/ISA/237) mailed on Sep. 26, 2022, by the European Patent Office as the International Searching Authority for International Application No. PCT/FR2022/050186, 12 pages.

*Primary Examiner* — Ariel A Balaoing
(74) *Attorney, Agent, or Firm* — BUCHANAN, INGERSOLL & ROONEY PC

(57) ABSTRACT

The invention relates to a method for displaying a visual reference in an image displayed by a viewing device masking all or some of the field of view of a user, said viewing device further comprising at least one movement sensor. The method defines a virtual tube around a viewing axis of the user, the walls of the tube corresponding to the peripheral visual field of the user. The visual reference comprises at least one frame and lines, the lines being placed on the walls of the tube. In response to a measurement of a rotational movement, the lines are modified to make a rotational movement about the viewing axis that is opposite the measured rotational movement and the frame is modified to make a rotational movement perpendicular to the viewing axis also opposite the measured rotational movement.

11 Claims, 7 Drawing Sheets

(56) References Cited

U.S. PATENT DOCUMENTS

| | | | |
|---|---|---|---|
| 2009/0040308 A1* | 2/2009 | Temovskiy | F41G 3/16 |
| | | | 382/296 |
| 2014/0267593 A1* | 9/2014 | Kim | H04N 23/698 |
| | | | 348/36 |
| 2016/0328827 A1* | 11/2016 | Ilic | G06T 3/4038 |
| 2017/0358141 A1* | 12/2017 | Stafford | G06T 7/246 |
| 2018/0196507 A1* | 7/2018 | Kim | G02B 27/0172 |
| 2019/0026944 A1* | 1/2019 | Laaksonen | G06F 3/012 |
| 2019/0061655 A1 | 2/2019 | Son | |
| 2019/0083739 A1* | 3/2019 | Jeannin | F21V 23/0492 |
| 2021/0318539 A1 | 10/2021 | Profendiner | |
| 2024/0223738 A1* | 7/2024 | Arimatsu | H04N 13/194 |

\* cited by examiner

METHOD FOR DISPLAYING A COMFORT-INCREASING AND ESPECIALLY ANTI-MOTION-SICKNESS VISUAL REFERENCE

TECHNICAL FIELD

The present invention relates to a method for displaying a comfort-increasing visual reference. More particularly, the invention applies to a screen covering all or part of the visual field, such as a virtual reality mask, a mixed reality mask, augmented reality glasses or a simulator screen.

TECHNOLOGICAL BACKGROUND

When a person is subjected to a difference of perception between their view and the inertial information that they perceive, in particular by means of their inner ear, said person can be susceptible to motion sickness, also known as travel sickness. Typically, the eye perceives a stable environment inside a moving object, for example inside a cabin of a moving ship, while the inner ear perceives conflicting information, i.e. information indicating that the ship is moving. This contradiction or difference of perception is the main cause of motion sickness.

Similarly, motion sickness can occur during the use of simulators and/or virtual reality masks. In this case, the information perceived by the inner ear and the information that the person sees can be in contradiction because only the visual perception of the person comes from the screen or screens located in their field of vision, which does not necessarily correspond to their movement, thus bringing the perception of the inner ear into contradiction with their vision.

Devices aiming to overcome motion sickness generally consist of providing a person with an item of inertial information in their peripheral field of vision. For this purpose, such devices have motion sensors making it possible to measure an item of position information measured spatially by the device. The item of position information measured is then translated into visual information displayed on one or more visualization elements placed in the peripheral field of vision of the person.

The patent application WO 2020/141269 discloses a device containing lateral screens displaying a simplified inertial matrix, synchronized with the movements measured by an inertial sensor integral with the screens. Such a system gives satisfactory results, but it is not always possible or sufficient to install it in a virtual or augmented reality mask. As the user's vision is captured by the main screen or screens situated in front of their eyes, this can sometimes cover part of the lateral vision of the user, preventing the use of lateral screens. Thus, such a system is not always usable or suitable for the use case. An additional or even replacement solution is desirable, in particular for certain virtual reality masks, or another application using one or more screens which would not allow, or not optimally, the use of the screens in the peripheral field of vision.

SUMMARY OF THE INVENTION

The invention proposes improving visual comfort for visualization devices for which the user has no or few external visual references making it possible to locate themselves spatially. For this purpose, the invention adds items of visual information superimposed on the displayed image or images in order to make a spatial tracking of the user possible.

More particularly, the invention proposes a method for displaying a visual reference in an image displayed by a visualization device masking all or part of the field of vision of a user, said visualization device moreover containing at least one motion sensor. The method contains the steps of:
  defining a virtual tube around a central axis of vision of the user, a distal opening of the tube corresponding to a focused visual field of the user, and the walls of the tube corresponding to the peripheral visual field of the user,
  defining at least one frame corresponding to an intersection between the virtual tube and a plane intersecting the central axis of vision,
  defining lines corresponding to the intersections between planes passing through the central axis of vision and the walls of the tube,
  creating a three-dimensional image corresponding to the at least one frame and to the parallel lines, and displaying said three-dimensional image as an overlay in the displayed image in order to have a visual reference in the displayed image.

According to the method, the three-dimensional image is modified in response to the measurement of a rotational movement by the at least one motion sensor, said measured rotational movement being broken down into a rotation measured around the central axis of vision and at least one rotation measured around an axis perpendicular to the central axis of vision, the method moreover containing the steps of:
  modifying the at least one frame by applying a rotational movement to the intersecting plane corresponding to said frame, said rotational movement being contrary to the at least one rotation measured around the axis perpendicular to the central axis of vision
  displacing the parallel lines around the central axis of vision according to a rotational movement contrary to the rotation measured around the central axis of vision.

To increase the perception of the visual reference, the definition of at least one frame can define a plurality of frames corresponding to intersections of planes parallel to each other and in which the parallel planes are affected by the same rotational movement.

According to a preferred embodiment, the motion sensor contains three linear accelerometers making it possible to measure a direction of gravity and in which the measured rotational movement corresponds to the rotation of the direction of gravity with respect to a reference direction of gravity.

In order to make an optimum efficiency possible over 360°, when the rotation measured around an axis perpendicular to the central axis of vision is greater than a critical angle, the intersecting plane or planes can be replaced with new intersecting planes having undergone a rotation of twice the critical angle.

To improve the perception of the visual reference, the display of the three-dimensional image can be effected with a colour and/or an intensity which varies over time. As a variant or in addition, the display of the three-dimensional image can also be effected with a colour and/or an intensity which varies as a function of the position of each pixel in the three-dimensional image.

To make it easier to visualize the displayed image, the central axis of vision can correspond to a direction of the user's gaze.

In the case of use of the method together with software displaying areas of interest, the central axis of vision can point at an area of interest of the displayed image.

In addition, the at least one motion sensor can measure a translational movement according to the central axis of vision in which the frame or frames can be displaced translationally along the central axis of vision in a direction contrary to the direction of the measured translational movement.

The at least one motion sensor can also measure a translational movement according to an axis perpendicular to the central axis of vision in which the lines can be displaced translationally in a direction contrary to the direction of the measured translational movement.

The invention also relates to a visualization device containing at least one screen masking all or part of the field of vision of a user, and at least one motion sensor which is integral with the screen. Said visualization device contains a central processing unit capable of storing and executing computer programs, in which one of the programs, when it is executed, performs said method.

BRIEF DESCRIPTION OF THE FIGURES

The invention will be better understood and other features and advantages thereof will become apparent on reading the following description of particular embodiments of the invention, given by way of illustrative and non-limitative examples, and with reference to the accompanying drawings, in which.

DETAILED DESCRIPTION

In the following detailed description of the accompanying drawings, identical elements are given identical identification references. Generally, these elements and their functionalities are described only once, for the sake of brevity in order to avoid repetitions. Furthermore, terms such as "to the left", "to the right", "at the top", "at the bottom", "in front of" or "behind" may be used in the description of the accompanying drawings. These terms generally refer to a particular location of a component or a direction of a movement of a component in a figure associated with or with respect to a user, which can vary from one figure to another.

Figure 1:
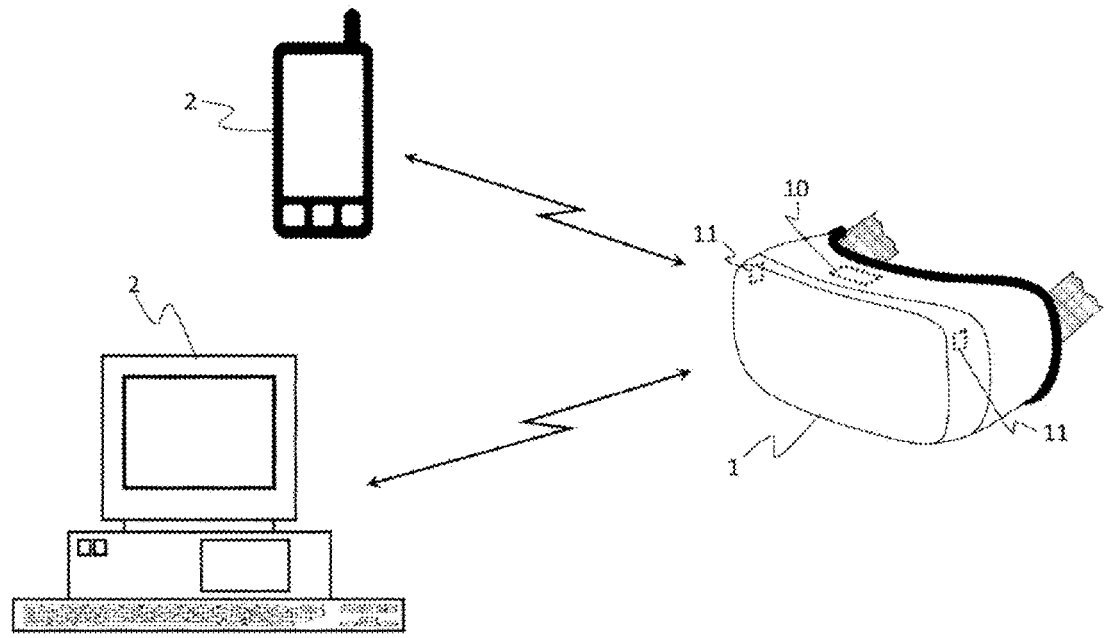
FIG. 1 shows an example of devices implementing the invention.

The invention applies to a visualization system masking all or part of the field of vision of a user. Such a system is represented for example in FIG. 1 and contains for example a virtual reality mask 1 which is autonomous or coupled to a processing unit 2, which can be a computer or a smartphone. The connection between the virtual reality mask 1 and the processing unit 2 can be a wireless connection or a wired connection, such as are known in the state of the art. The virtual reality mask 1 can contain a central screen or one screen for each eye, depending on whether it is desired to display an image with or without relief. To implement the invention, the mask 1 must be equipped with a motion sensor 10. In a particular embodiment, the mask 1 can also be equipped with an eye-tracking sensor 11.

The motion sensor 10 can be of different types, it can be constituted by an inertial unit, accelerometers or interactive sensor unit making it possible to locate the spatial position of said mask 1 inside a room which is equipped with beacons interacting with the interactive sensors. All of these sensor technologies are known, as well as others, it being important that the motion sensor 10 can measure a movement felt by the wearer of the mask 1.

However, in a preferred embodiment, the motion sensor 10 is constituted by three linear accelerometers making it possible to determine a direction of gravity experienced by the virtual reality mask. On the basis of this direction of gravity experienced, angles of rotation are calculated according to the three axes of the accelerometers with respect to a reference direction of gravity recorded in an initialization position of the mask 1.

The invention is not limited to a virtual reality mask and applies to any type of visualization means masking all or part of the field of vision of the user. By way of example, the virtual reality mask can be replaced with augmented reality glasses, which the user will wear in particular in a vehicle in order to benefit from an inertial tracking inside said vehicle. According to another example, the visualization system can be a simulator imitating for example the cockpit of a car or an airplane and surrounded by a screen showing scrolling images consistent with the supposed movement of said simulator, but which can be inconsistent with a movement perceived by the user. In order to conform to the invention, said glasses or said simulator must also be equipped with a motion sensor making it possible to measure a movement undergone by said glasses or said simulator.

Figure 2:
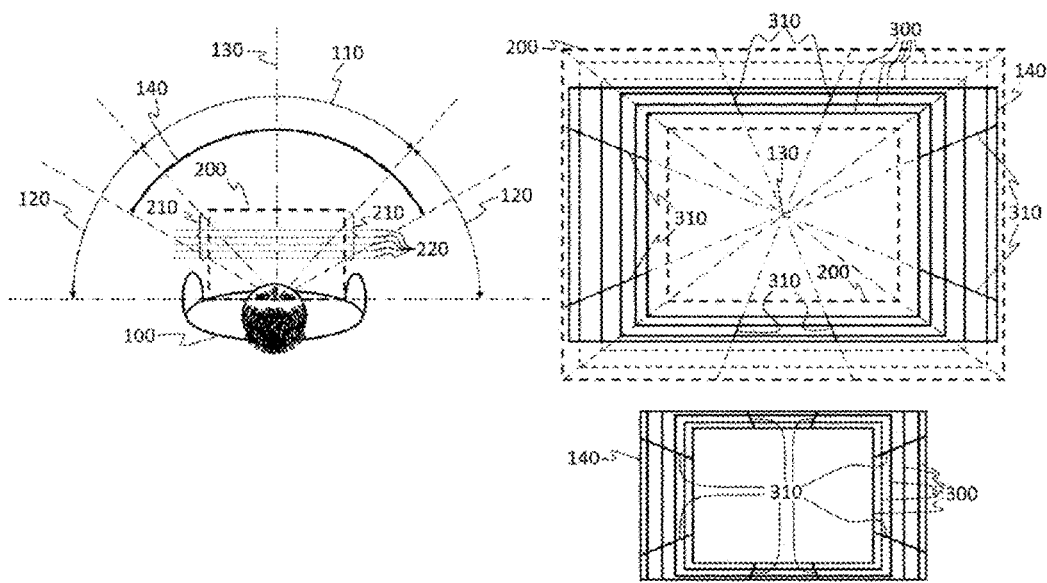
FIG. 2 illustrates the principle and the structure of a visual reference according to the invention in the initial position.

The invention aims to add a visual reference as an overlay in the image displayed on the screen or screens of the mask 1. The principle implemented by the invention, as well as the structure of the visual reference, will now be described in detail with the aid of FIGS. 2 to 7, which each show, in a top part of the figures, a spatial positioning of the user on the left and the structure of the visual reference corresponding to the positioning of the user on the right. The bottom part of FIGS. 2 to 7 shows the visual reference as it will be displayed as an overlay on the screen which is displaying the visualized image. FIG. 2 illustrates an initial or initialization positioning of the device which can be performed when the device is turned on or when requested by the user, for example when the user sits down inside a vehicle, puts on their mask 1 and prepares to start playing a film or running a game.

The right-hand part of FIG. 2 shows the organization of the visual function of a field of vision of a user 100 of the mask 1. The field of vision at least essentially forms a half sphere which is constituted by a central field of vision 110 and a lateral field of vision 120 or peripheral field of vision. The central field of vision 110 is centred on a central axis of vision 130 aimed at by the user 100 and the opening angle of which around the central axis of vision 130 depends on the depth of field aimed at by the user 100.

The mask 1 is placed in the field of vision of the user 100 and has an area of screen 140 which covers the whole of the central field of vision 110 and part of the lateral field of vision 120. The screen 140 is visualized on the left-hand part of FIG. 2 in order to show the inertial reference to be displayed and how the latter is constructed.

The central field of vision 110 forms the subject of the voluntary reading by the user 100. The lateral field of vision 120 is dedicated to the inertial visual tracking, to the visual discrimination of the movements, to the visual balance, and thus also to the stabilization of the central field of vision 110. The lateral field of vision 120 contributes to the inertial analysis of the visual field by cooperating with other functions, in particular of the (inertial) vestibular system of the inner ear of the user 100. Nevertheless, items of inertial information can also be retrieved through the central field of vision 110. Moreover, the voluntary reading is essentially based on the central field of vision 110 but still retrieves an array of information through the peripheral field of vision. The central and voluntary analysis also relies on the 30) peripheral analysis to discern for example other movements in a general movement of the user 100.

According to an embodiment example of the present invention, the central field of vision 110 and part of the lateral field of vision 120 are displayed on the screen 140 of the mask 1. The invention proposes adding items of inertial information into the part of the lateral field of vision 120 of the screen over a virtual tube 200, for example with a rectangular cross section surrounding the central axis of vision 130 of the user 100. An opening of the tube 200 corresponds to a focused visual field of the user which is substantially equal to or slightly smaller than the central field of vision 110. The walls 210 of the tube 200 correspond to the lateral visual field 120 of the user 100 and can comprise a small part of the central field of vision 110. The walls 210 serve to support the items of inertial information of the visual reference of the invention. A three-dimensional projection of the items of inertial information of the tube 200 is then embedded as an overlay on the image visualized on the screen.

The items of inertial information according to the invention consist of one or more frames 300 and vanishing lines 310 parallel to the central axis of vision 130, as shown in the left-hand part of FIG. 2. According to the invention, the tube 200 remains integral with the central axis of vision and only serves to support the items of inertial information.

The frames 300 are defined on the basis of the intersection between the walls 210 of the tube 200 and planes 220 intersecting the central axis of vision 130. If several frames 300 are used, the intersecting planes 220 are planes parallel to each other. Preferably, during initialization of the device, the intersecting planes 220 are fixed in order to be perpendicular to the central axis of vision 130, as shown in FIG. 2. Once the position of the intersecting planes 220 has been determined during the initialization, they remain spatially fixed. The three-dimensional projection of the frames 300 corresponds to a stacking of frames, the spacing of which corresponds to a perspective effect.

The vanishing lines 310 correspond to the intersections between planes passing through the central axis of vision 130 and the walls of the tube 200. The planes defining the vanishing lines 310 are preferably spaced apart angularly and regularly. The length of the vanishing lines 310 can be limited such that they remain comprised within the lateral field of vision. When the vanishing lines 310 are projected three-dimensionally into the image, they converge towards one and the same vanishing point corresponding to the central axis of vision 130.

The three-dimensional projection of the frames 300 and the vanishing lines 310 makes it possible for the user to mark out an inertial reference in the form of a perspective matrix surrounding the central field of vision 110.

The system having been initialized in accordance with the configuration from FIG. 2, it should now be indicated how the inertial reference reacts as a function of measured movements. The motion sensor 10 makes it possible to measure the movements of the mask 1 which correspond to movements of the head of the user 100.

Figure 3:
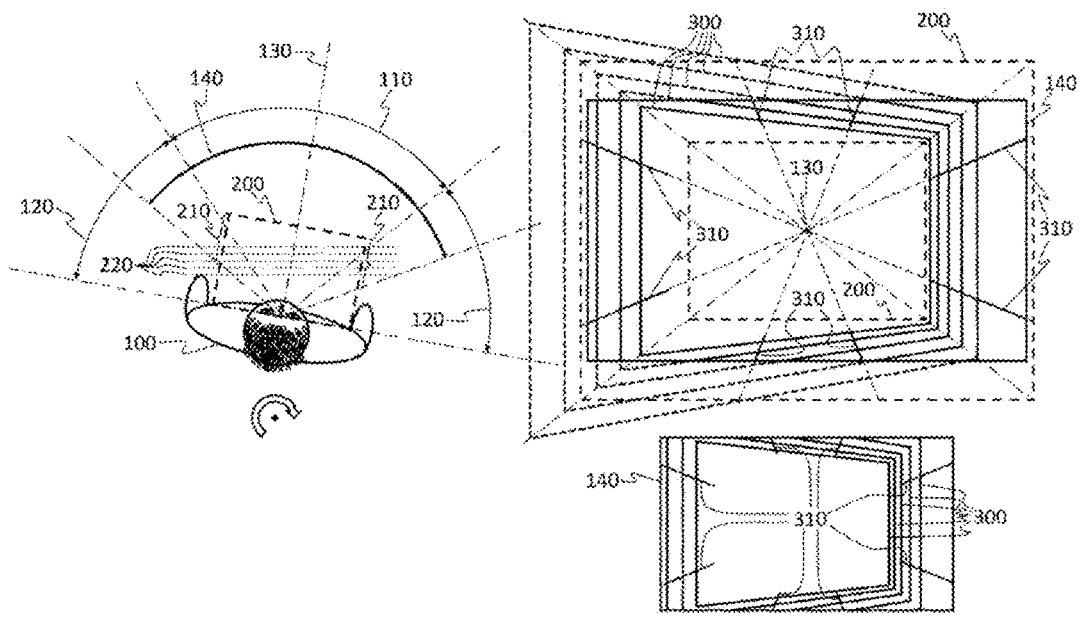
FIG. 3 illustrates a modification of the visual reference of the invention when the user is subjected to a physical rotation according to a first axis.

FIG. 3 illustrates a rotational movement of the user 100 towards the right, and therefore a rotation of the mask 1. Such a rotation towards the right can be due to the vehicle inside which the user is located and can only be perceived by them thanks to the inertial reference of the invention.

As shown in the right-hand part of FIG. 3, the rotation of the head of the user 100 drives the rotation of the mask 1, and therefore of the central axis of vision 130 as well as of the central field of vision 110 and of the lateral field of vision 120 and of the field covered by the screen 140. As indicated previously, the tube 200 is centred on the central axis of vision 130 and therefore follows the rotational movement towards the right. In contrast, the intersecting planes 220 remain spatially fixed. The intersections of said intersecting planes 220 with the walls of the tube 200 correspond to frames 300 which have carried out a rotation with respect to the tube 200 towards the left by the same angle as the rotation to the right.

The three-dimensional projection of the rotation is shown on the right-hand side of FIG. 3. The left-hand side of the frames 300 widens to the point of no longer appearing on the screen, whereas the right-hand part of the frames 300 narrows as it approaches the distal opening of the tube 200. Thus, the user perceives, in their lateral field of vision, a deformation of the frames which indicates to them that their head is turning towards the right with respect to said frames 300. This makes it possible for the user to have a consistency between the perception of the inner ear and the perception of their peripheral vision.

Figure 4:
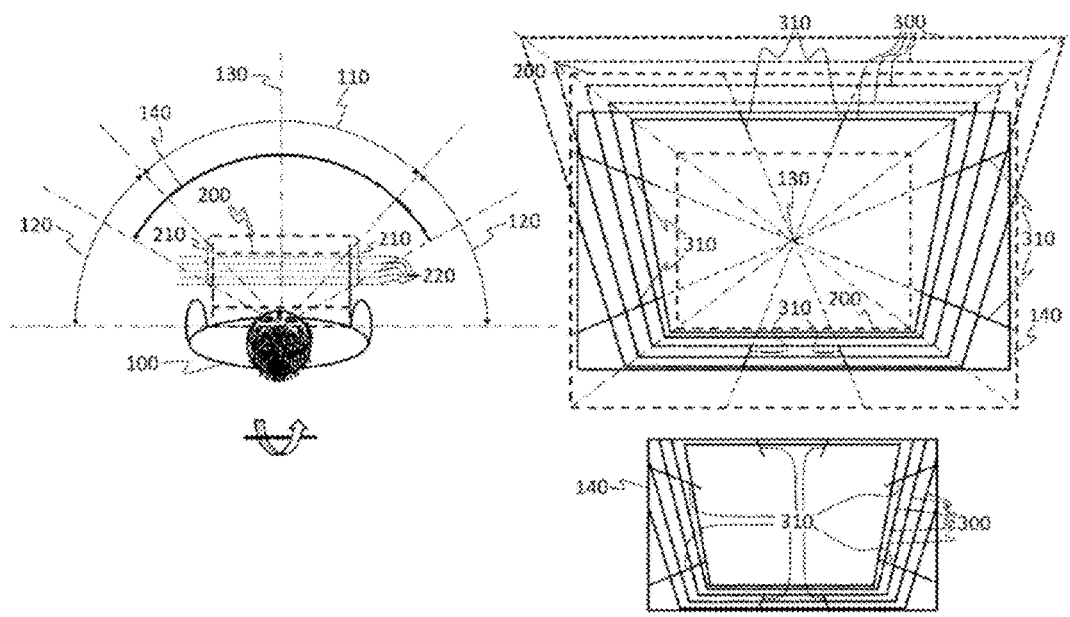
FIG. 4 illustrates a modification of the visual reference of the invention when the user is subjected to a physical rotation according to a second axis.

FIG. 4 illustrates a rotational movement of the user 100 downwards, and therefore a rotation of the mask 1. Such a rotation downwards corresponds to a pitching movement of a vehicle inside which the user is located which the latter can only perceive thanks to the inertial reference of the invention.

As shown in the right-hand part of FIG. 4, the rotation of the head of the user 100 drives the rotation downwards of the mask 1, and therefore of the central axis of vision 130 and of the tube 200. In contrast, the intersecting planes 220 remain spatially fixed. The intersections of said intersecting planes 220 with the walls of the tube 200 correspond to frames 300 which have carried out a rotation with respect to the tube 200 upwards by the same angle as the rotation downwards.

The three-dimensional projection of the rotation is shown on the right-hand side of FIG. 4. The top of the frames 300 widens to the point of no longer appearing on the screen, whereas the bottom of the frames 300 narrows as it approaches the distal opening of the tube 200. Thus, the user perceives, in their lateral field of vision, a deformation of the frames which indicates to them that their head is turning downwards with respect to said frames 300.

Figure 5:
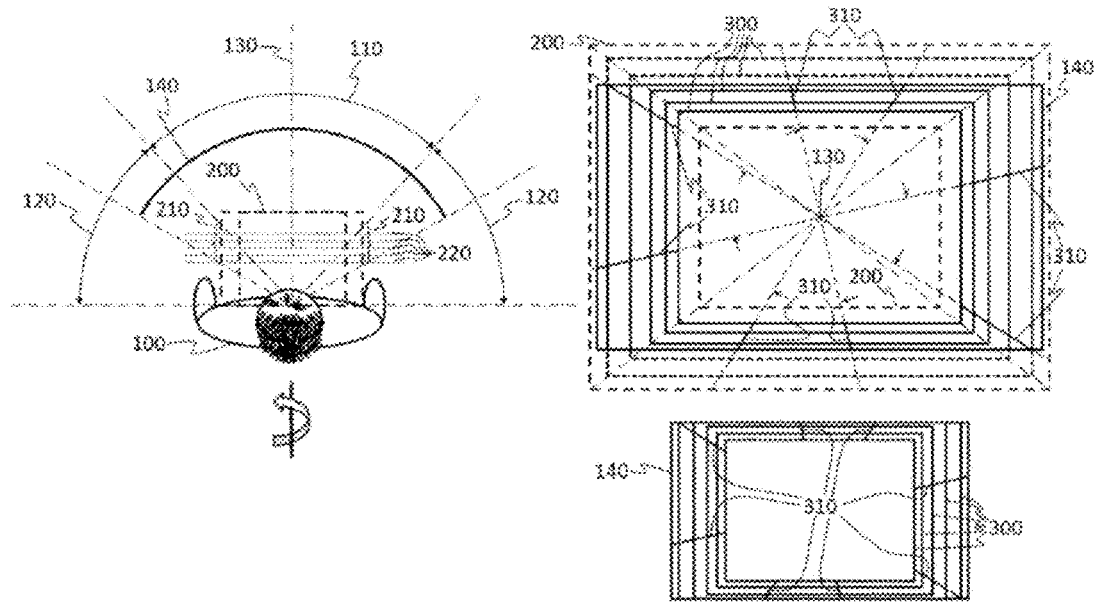
FIG. 5 illustrates a modification of the visual reference of the invention when the user is subjected to a physical rotation according to a third axis.

FIG. 5 illustrates a rotational movement of the user 100 in the anti-clockwise direction according to the central axis of vision 130, therefore a rotation of the mask 1. Such a rotation corresponds to a rolling movement of a vehicle inside which the user is located which the latter can only perceive thanks to the inertial reference of the invention.

The right-hand part of FIG. 5, which is a view from above, only shows a rotation of the tube 200 around the central axis of vision 130. In contrast, the intersecting planes 220 remain spatially fixed. The intersections of the intersecting planes 220 with the walls of the tube 200 correspond to frames 300 which are unchanged with respect to the frames 300 from FIG. 2. However, the vanishing lines 310 are displaced by carrying out a rotation in the clockwise direction around the central axis of vision 130.

Figure 6:
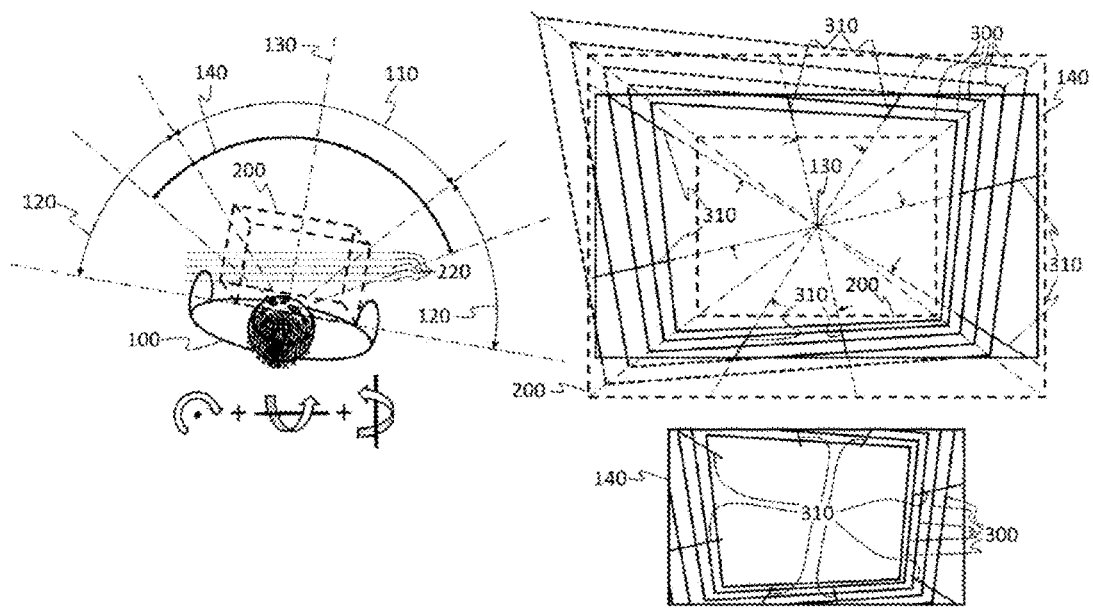
FIG. 6 illustrates a modification of the visual reference of the invention when the user is subjected to a physical rotation according to the first to third axes.

The rotations can of course be combined with each other. FIG. 6 illustrates a combination of rotational movements of the user 100 towards the right, downwards and around the central axis 130 in the anticlockwise direction. Such a combination of rotations breaks down into a rotation around the central axis of vision 130 and a rotation around an axis perpendicular to the central axis of vision 130. The rotation around the axis perpendicular to the central axis of vision 130 can also be broken down into two rotations perpendicular to each other.

The rotation or rotations around one or two axes perpendicular to the central axis of vision cause modifications of the frames by rotation of the intersecting planes 220 according to one or two axes of rotation by applying a rotational movement which is inverted with respect to the measured rotational movement. Thus, in the example of FIG. 6, the bottom right corners of the frames 300 move closer to the distal opening of the tube 200 while the upper left corner moves away from the distal part, thus causing part of the frames 300 to leave the visualization screen 140. The rotation around the central axis of vision 130 is used to displace the vanishing lines 310 around the central axis of vision 130 according to a rotational movement contrary to the measured rotation. The combination of these two movements in the lateral field of vision of the user 100 makes it possible for the latter to identify all of the rotational movements that they perceive with the aid of their inner ear.

As described in detail previously, the system effectively makes it possible for a user to easily be able to visually get their bearings spatially with respect to their sensation. However, such a system is really only effective if the angles of rotation of the frames make it possible to always visualize at least one side of a frame in the peripheral field of vision. If the rotation of the frame is too great, the frame edges can be located in the central field of vision, which is not desirable as they would become invisible in order to avoid disrupting the voluntary reading of the image in the central field of vision 110.

In order to make a rotation of the user over 360 degrees possible while keeping the support of the frames 300 in their peripheral vision, it is possible to define a critical angle $\alpha_{crit}$ from which a change of reference is carried out. In the described example, the critical angle $\alpha_{crit}$ can correspond to the rotational position for which there remains only one frame 330 which is not yet at the level of the distal part of the tube 200. As a variant, the critical angle $\alpha_{crit}$ can correspond to the rotational position for which a first frame 330 reaches the distal part of the tube 200. The change of reference consists of replacing the intersecting planes 220 with new intersecting planes 221 having been subjected to a rotation of twice the critical angle. The new intersecting planes 221 then make it possible to define new frames 301 corresponding to this new frame of reference, which inverts the position of the frames 301 with respect to the distal opening of the tube 200. It then becomes possible to continue the rotation with the aid of the frames 301, while keeping a maximum of inertial information for the user 100.

Figure 7:
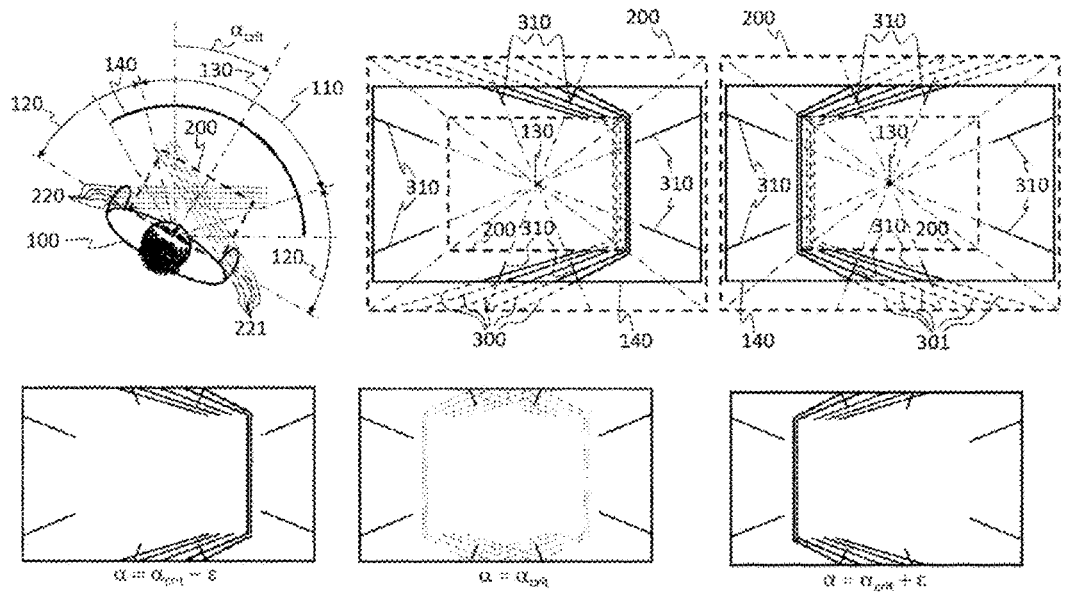
FIG. 7 illustrates a modification of the visual reference of the invention when the user is subjected to a very large physical rotation according to the first axis.

The transition from the frames 300 to the frames 301 can be effected in a "cross dissolve" as illustrated at the bottom of FIG. 7. When the measured angle of rotation increases and approaches the critical angle $\alpha_{crit}$, the intensity of visualization of the frames 300 should be decreased while the intensity of visualization of the frames 301 progressively increases. Thus, when at the critical angle $\alpha_{crit}$, the frames 300 and 301 are visualized simultaneously with a lower intensity of visualization. If the angle of rotation continues to increase, the intensity of visualization of the frames 300 continues to decrease until becoming invisible, while the frames 301 increase their intensity of visualization up to a nominal intensity.

Figure 8:
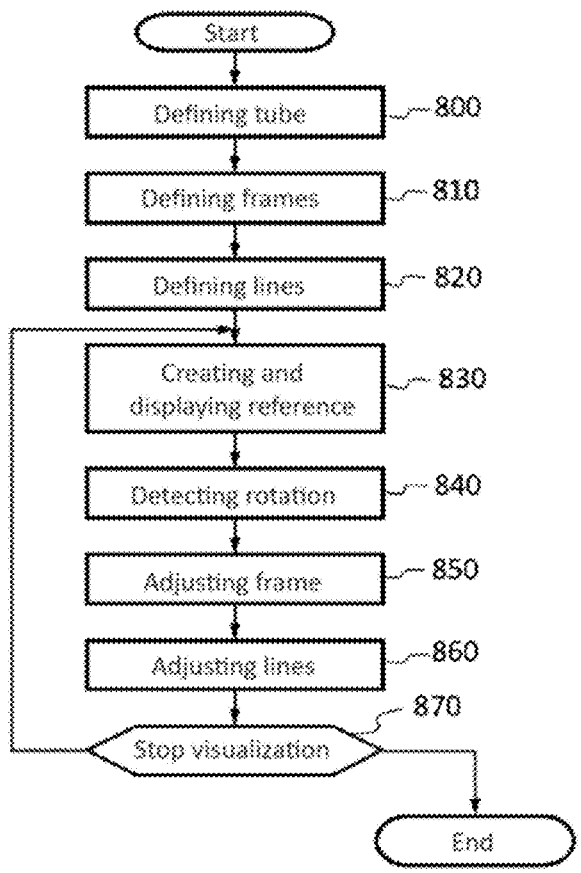
FIG. 8 shows an operating flowchart of the invention.

The different principles of construction of the visual reference having been described, the implementation by the processing unit for producing and displaying said visual reference should be described in detail. FIG. 8 represents a method of operation of software implemented by the processing unit.

The software can be started by the user directly (by entering a command) or indirectly (for example at the start of the playing of a film, execution of a video game or of a simulation). The method implemented begins with initialization steps. Step 800 consists of recording, as zero reference angle, the angle measured by the motion sensor 10 during the start-up, then of constructing the virtual tube 200 around the central axis of vision 130 which is, for example, an axis normal to the centre of the screen. The virtual tube 200 must have a distal opening placed at a certain distance from the user which corresponds to an opening centred around the central axis of vision 130 and which corresponds substantially to the focused field of vision of the user 100. By focused field is meant the area of interest of the image which the user has to look at without being disturbed by inertial references. The walls of the tube 200 which are parallel to the central visualization axis 130 correspond to a peripheral or lateral visual field 120 of the user, in order to display the items of inertial information on said walls.

Once the tube has been defined, a step 810 defines one or more frames 300 supported by one or more intersecting planes 220. The intersecting planes 220 can be placed arbitrarily as long as they are parallel to each other and intersecting with respect to the central axis of vision 130. However, it is preferred to choose intersecting planes 220 which are perpendicular to the central axis of vision 130 when the measured angle is equal to the reference angle. The intersecting planes 220 can be equidistant to each other and distributed along the central visualization axis 130 over all or part of the tube 200. The frames 300 correspond to the intersections between the walls of the tube 200 and said intersecting planes 220.

A step 820 of defining the vanishing lines 310 can be performed before or after step 810. The definition of the vanishing lines 310 consists of fixing a number of vanishing lines 310, for example eight, and of distributing them over the walls of the tube 200 by spacing them apart so as to have a homogeneous distribution over the walls of the tube. A homogeneous distribution can be effected by spacing the lines apart angularly around the central axis of vision 130.

Once steps 810 and 820 have been performed, a three-dimensional image of the frames and vanishing lines is created then displayed as an overlay on a visualized image, for example the current image of the film during a step 830. The overlaying can be effected for example by replacing the points of the visualized image which correspond to the frames 300 and to the vanishing lines 310 with points of a predetermined colour and luminosity.

After the display of the image, a detection of rotation 840 is carried out. Such a detection can be performed in a synchronized manner each time that an image is displayed on the screen 140. The detection consists of reading an angle of rotation of the visualization device, for example of the mask 1, measured by the motion sensor 10. This measured angle corresponds to a positioning angle of the device and therefore an angle sensed indirectly by the user 100. The measured angle is then compared with the reference angle recorded during step 810 in order to obtain an angular difference between the reference angle and the measured angle. The angular difference is broken down into a first angle of rotation around the central axis of vision 130 and a second angle of rotation around an axis perpendicular to the central axis of vision 130.

Once step 840 has been performed, a step 850 of adjusting the frames is performed. For the sake of simplifying the calculation, rather than recalculating the positions of the tube with respect to spatially fixed planes, as explained with the aid of FIGS. 2 to 7, it is possible to transpose the movement to a simple rotation of the planes around the point of intersection with the central axis of vision 130. The frames are then defined as being the intersection between the walls of the tube 200 and the planes 220 to which a rotation is applied which is contrary to the second angle which was calculated during step 840. By contrary rotation is meant a rotation which has an angle with the same amplitude but with the opposite sign.

Step 850 can also take the critical angle $\alpha_{crit}$ into consideration. Thus, when the second angle is close to the critical angle $\alpha_{crit}$, a second reference angle is determined, the second reference angle being equal to the reference angle plus twice the critical angle $\alpha_{crit}$. First frames 300 are calculated with the recorded reference angle and second frames 301 are calculated with the second reference angle. Two visualization intensity coefficients are also determined as a function of the difference between the second measured angle on the one hand and the recorded reference angle and the second reference angle on the other hand. If the second measured angle is greater (in absolute values) than the critical angle $\alpha_{crit}$, then the second reference angle is recorded in order to become the new recorded reference angle.

A step 860 of adjusting the lines is also performed after step 840, before or after step 850. The step 860 of adjusting the lines consists of displacing the vanishing lines 310 along the walls of the tube 200 around the central axis of vision 130 according to a rotational movement contrary to the first rotation calculated in step 840.

Once steps 850 and 860 have been performed, a test 870 verifies that the visualization of the visual reference is still active. If the visualization is no longer active, then the program stops. If the visualization is still active, then the process continues by returning to step 830. However, if first frames 300 and second frames 301 have been defined, they are displayed with an intensity proportional to the visualization intensity coefficients.

Variants and improvements are possible. In particular, the second angle calculated in step 840 can be broken down into two components according to two axes perpendicular to each other. If two components are used, the rotation calculations of step 850 can be effected according to each of the two components. The management of the critical angle can also be effected according to each of the two components, the angle being able to be critical on one of the components without being critical on the other component. A person skilled in the art will then understand that the calculation of the second reference angle will then be effected only according to the component which is at the critical angle. Moreover, the use of two components can make it possible to have two critical angles peculiar to each of the components.

The display indicated in step 830 can be effected with thicker or thinner lines at the choice of the person skilled in the art, or even with thicknesses that differ between the frames 300 and the vanishing lines 310. The colour and the intensity of display can also be adjusted as a function of the visualized image, each pixel of the frames or of the vanishing lines being able to have a colour and an intensity corresponding to a maximum contrast vis-à-vis the displayed image. Another display variant can consist of having variations in intensity and/or colour in order to increase the perception by the user. The variations in intensity and/or colour can be determined as a function of time. The intensity can vary as a function of time according to a sine function or other mathematical function making it possible to obtain various flicker effects. A sine function on the colours will have the effect of changing the colours of the reference over time. Another possibility is to have a medium, low or zero intensity on the majority of the images and an intensity peak on one image, for example every second or half second, in order to have a visualization flash effect.

Again to increase the perception by the user, the colour and intensity of the display can vary as a function of time and the position of the pixels. By way of example, the application of a sine function to the colour of each pixel as a function of time and the position of said pixel makes it possible to obtain rainbow-coloured frames and lines which flicker. Another possibility can consist of having a medium luminosity on the pixels of the frames and vanishing lines and having a spot of greater intensity which moves. This can be realized by defining, for each displayed image, a line of pixels where the intensity is greater, changing lines at each image display.

Moreover, depending on whether the display is effected on one screen or on two screens in order to have an image in relief, a person skilled in the art will take care to make a perspective projection of the frames and vanishing lines.

Figure 9:
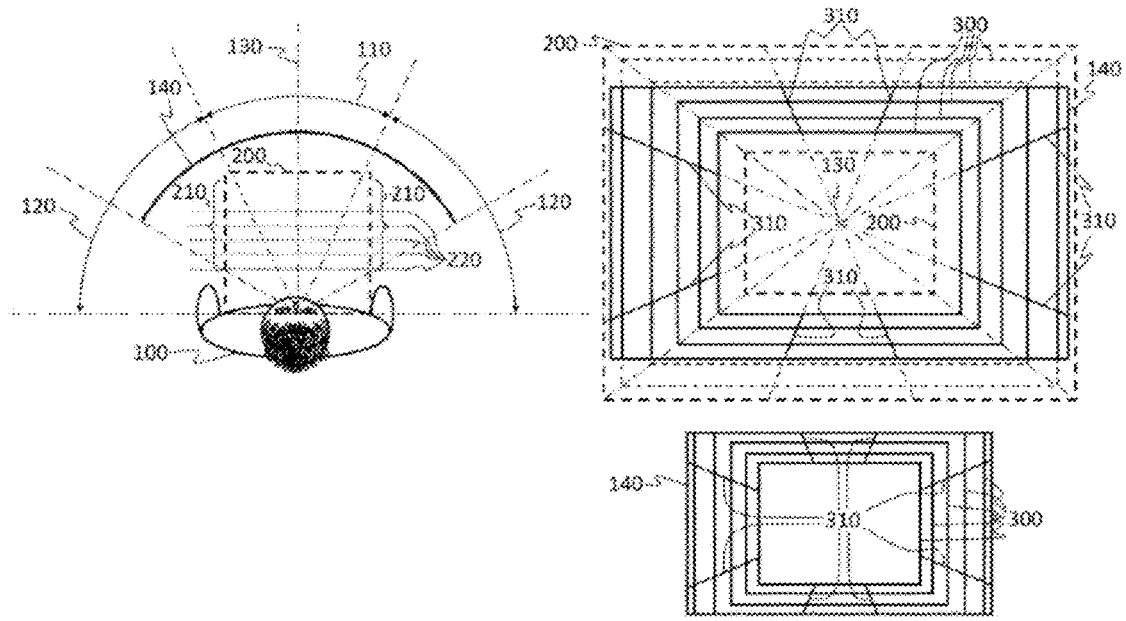
FIG. 9 illustrates a first type of variant of the visual reference of FIG. 1.

Other improvements can also be made to the invention. In particular, the tube 200 is defined as a function of the focused image of the user. This focused image corresponds to a central field of vision corresponding to an opening of approximately 120° in a fixed environment. The opening can also be adjusted as a function of preferences of the user or as a function of dynamic parameters linked to what the user is looking at. By way of example, if the environment is in motion or if the person is looking far away, the central field of vision is reduced, as shown in FIG. 9. Such a shrinking of the field of vision can be linked to the displayed image as a function of the depth of field or a running speed of the image, for example if the displayed image corresponds to a car race simulation. In this case, the tube 200 should be adjusted as a function of the desired focusing. To mark out the change in focusing, the intersecting planes 220 must be displaced in proportion to the lengthening of the tube 200. Such a displacement makes it possible to replace the lateral tracking in the lateral field of vision which has been widened. The software which displays the image should then communicate a focusing distance in order that the method of the invention can adjust the position of the frames 300 accordingly as a function of this focusing.

In addition, in the preceding examples, the central axis of vision 130 is placed in the centre of the screen 140. It is possible that this central axis of vision 130 can shift in the screen. It is in particular possible that the software displaying the image desires to attract the attention of the user to a precise point of the image, and in this case it is preferable to focus the gaze of the user 100 on the desired area of interest.

Another possibility is to adapt the central axis of vision 130 dynamically to the gaze of the user. For this purpose, the mask 1 must be equipped with eye-tracking sensors 11. The gaze direction information given by the sensors determines a point at which to aim in the screen and it then becomes possible to adjust the invention as a function of the gaze of the user.

Figure 10:
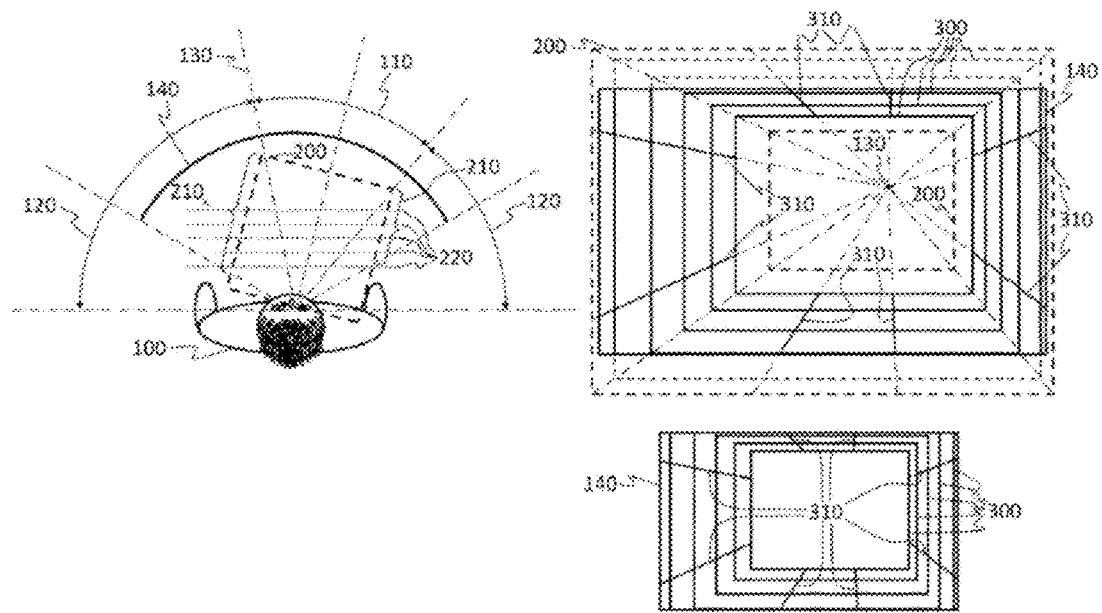
FIG. 10 illustrates a modification of the visual reference as a function of a point of interest in the image.

FIG. 10 shows a modification of the central axis of vision 130 and the changes which result from it. The tube 200 follows the central axis of vision 130. However, the field of the screen 140 remains immobile, which translates visually into a displacement of the walls of the tube 200 in the left-hand part of FIG. 10. However, if no rotation of the user has been carried out, the frames 300 only carry out a translation in order to correspond to the walls of the tube 200, without showing any rotational movement.

Figure 11:
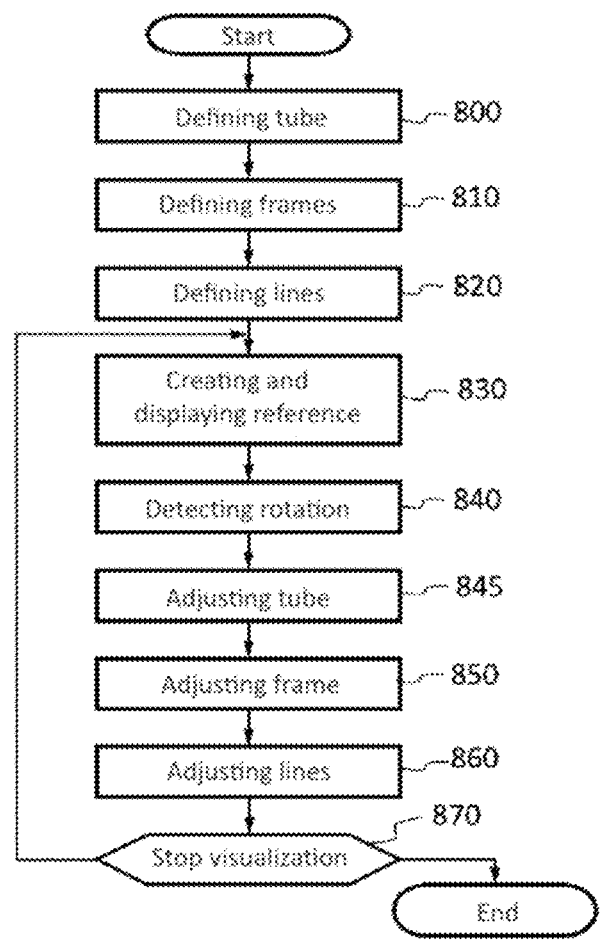
FIG. 11 shows a variant of the operating flowchart of FIG. 8.

To take account of the modifications linked to the management of the focusing distance and to a possible change of central axis of vision 130, the method for implementing the invention has to be modified as indicated in FIG. 11 by adding a step 845 of adjusting the tube 200 after the step 840 of detecting rotation and before the steps 850 and 860 of adjusting the frames 300 and the vanishing lines 310. Moreover, in step 810, it is then preferable that the intersecting planes 220 are not perpendicular to the central visualization axis but are preferably perpendicular to an axis perpendicular to the centre of the screen 140. Equally, the step 840 of detecting rotation has to be modified such that the first angle corresponds to a rotation around an axis perpendicular to the centre of the screen 140 and the second angle corresponds to a rotation in a plane parallel to the plane or to a middle plane of the screen 140.

The step 145 of adjusting the tube 200 consists of retrieving an item of focusing distance information and/or an item of gaze angle information. These items of focusing distance information and/or an item of gaze angle information can originate from game software which indicates them as a function of the displayed image, a measurement of the direction of the gaze, or even a combination of the two when the displayed image is a three-dimensional image and the gaze is aimed at an area of the screen more or less far away. The item of gaze angle information makes it possible to define the position of a main axis of vision. A virtual tube 200 is then constructed around the central axis of vision over a length corresponding to the focusing distance. Once the central axis of vision 130 and the tube 200 have been redefined, the adjustment of the frames 300 and the vanishing lines 310 is effected by taking account of the direction of the gaze and the focusing distance.

Figure 12:
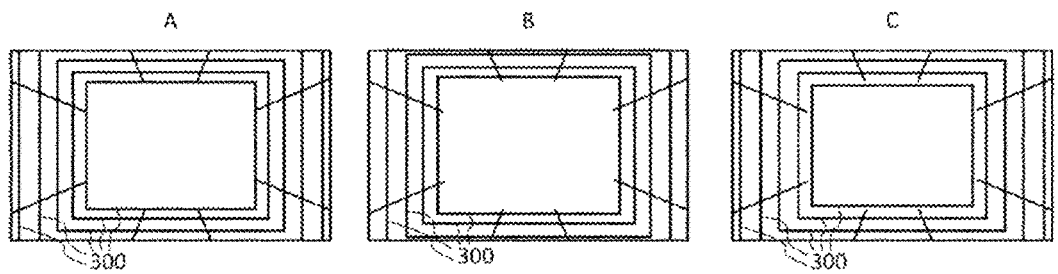
FIG. 12 shows a translational movement being taken into account by the visual reference according to the first axis.

Another improvement can consist of taking account of translational movements of the user. FIG. 12 illustrates the movement performed by the frames 300 when a translational movement is performed forwards according to the central axis of vision 130 or the axis perpendicular to the centre of the screen 140. The images labelled A, B and C correspond to the sequence of visualization in the course of the translation in the central axis of vision 130. Image A corresponds to the initial position, which conforms to the rest position of FIG. 2. Image B corresponds to a first translation forwards during which the frames 300 widen, which corresponds to a retreat of said frames backwards, the largest frame having disappeared from the screen. If this translation forwards is continued, the frames continue to widen up to a position C, where, the frames having moved back significantly, a new frame appears at the level of the opening of the tube 200 (not represented in FIG. 12).

Figure 13:
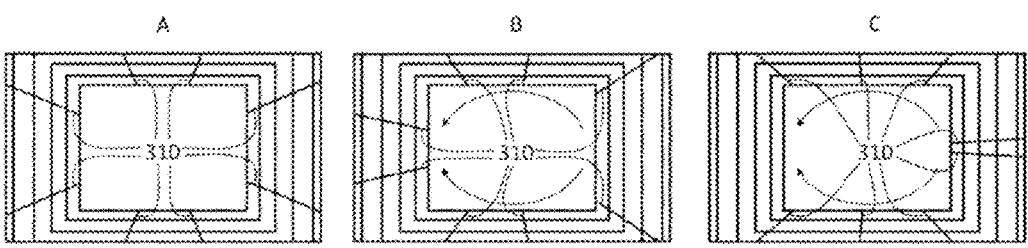
FIG. 13 shows a translational movement being taken into account by the visual reference according to the second axis.

FIG. 13 illustrates the movement performed by the vanishing lines 310 when a translational movement is performed towards the right, perpendicularly to the central axis of vision 130. The images labelled A, B and C correspond to a sequence of visualization performed in the course of the translation towards the right. Image A corresponds to the initial position, which conforms to the rest position of FIG. 2. Image B corresponds to a first translation towards the right, during which the vanishing lines 310 of the upper part carry out an anti-clockwise rotation, while the vanishing lines 310 of the lower part carry out a rotation in the clockwise direction. The combination of these two rotations simulates a translation of the vanishing lines towards the left, being contrary to the measured translational movement. If the translational movement towards the right is continued, the two rotations continue, but when an upper or lower vanishing line 310 reaches the middle of the screen on the left, it disappears and a new vanishing line 310 appears on the opposite side of the screen 140 to the right, as shown in image C.

Figure 14:
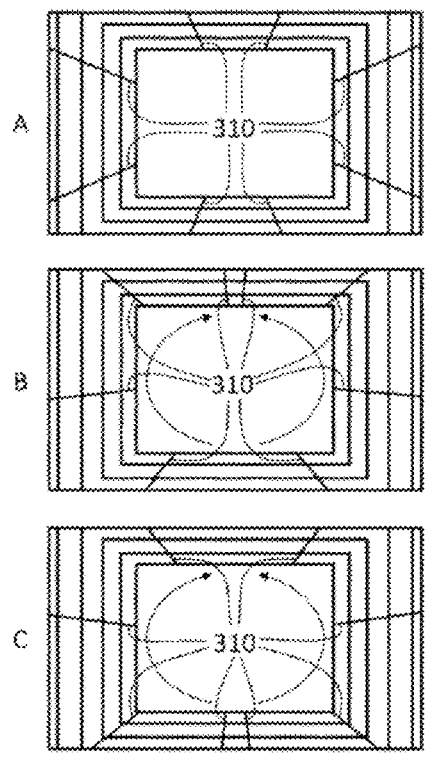
FIG. 14 shows a translational movement being taken into account by the visual reference according to the third axis.

FIG. 14 illustrates the movement performed by the vanishing lines 310 when a translational movement is performed downwards, perpendicularly to the central axis of vision 130. The images labelled A, B and C correspond to visualization times during the translation downwards. Image A corresponds to the initial position, which conforms to the rest position of FIG. 2. Image B corresponds to a first translation downwards, during which the vanishing lines 310 of the right-hand part carry out an anti-clockwise rotation, while the vanishing lines 310 of the left-hand part carry out a rotation in the clockwise direction. The combination of these two rotations simulates a translation of the vanishing lines upwards, being contrary to the measured translational movement. If the translational movement downwards continues, the two rotations continue, but when a vanishing line 310 situated to the right or to the left reaches the top middle of the screen 140, it disappears and a new vanishing line 310 appears on the opposite side, at the bottom of the screen, as shown in image C.

Although this is not necessary, the translational movements can be combined with the rotational movements in order to have a rendering closest to the sensation of the user. Nevertheless, when the translational movements of the vanishing lines 310 are combined with the rotational movement of the vanishing lines, it is possible that the distribution of said lines 310 is no longer homogeneous on the screen 140. In order to remedy this, it can be envisaged to reinitialize the vanishing lines 310 regularly, for example every 2 to 10 seconds. The reinitialization can consist of replacing the lines with angles which are equidistant around the central axis of vision 130 on the walls of the tube 200. This reinitialization can possibly be carried out by "cross dissolve".

Figure 15:
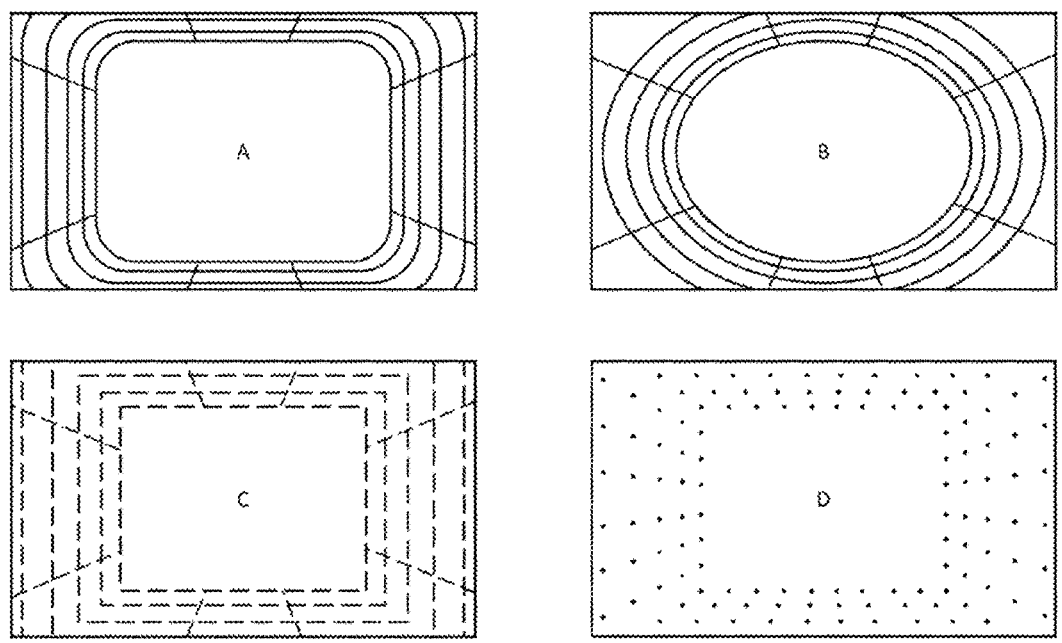
FIG. 15 shows variants of the shape of the visual reference according to the invention.

The different examples have been realized with a tube with a rectangular cross section in order to simplify the explanations given. Similarly, the visualization of the visual reference is performed with the aid of continuous lines, which correspond to the frames and to the vanishing lines. A number of other variants are possible. By way of example, FIG. 15 illustrates four variants, labelled A, B, C and D. First of all, it should be noted that the tube 200 can be considered as a mathematical cylinder with any base, projected according to the central axis of vision 130. The base of the cylinder can have any shape whatever and transmit this shape to the frames. By way of example, the base of the cylinder and the frames can have the shape of a rectangle with rounded corners, corresponding to image A, or an ovoid, corresponding to image B, or another geometric shape. In order to accentuate or reduce the perspective effect, the tube can also be a truncated cone opening or closing at the level of the distal part. Equally, the representation of the frames and of the vanishing lines is not necessarily performed with the aid of continuous lines. Image C shows a display of the frames and vanishing lines with the aid of broken lines. Image D shows another display variant using only points placed on the frames, the points being able to be aligned on the vanishing lines. The display variants are not limited to those shown in the present description and a person skilled in the art will be able to imagine a number of other representations without departing from the scope of the invention as defined in the accompanying claims.

The invention claimed is:

1. Method for displaying a visual reference in an image displayed by a visualization device masking all or part of the field of vision of a user, said visualization device moreover containing at least one motion sensor, wherein the method contains the steps of:
    defining a virtual tube around a central axis of vision of the user, a distal opening of the tube corresponding to a focused visual field of the user, and the walls of the tube corresponding to the peripheral visual field of the user,
    defining at least one frame corresponding to an intersection between the virtual tube and a plane intersecting the central axis of vision,
    defining lines corresponding to the intersections between planes passing through the central axis of vision and the walls of the tube,
    creating a three-dimensional image corresponding to the at least one frame and to the lines, and displaying said three-dimensional image as an overlay in a displayed image in order to have a visual reference in said displayed image;
in which the three-dimensional image is modified in response to the measurement of a rotational movement by the at least one motion sensor, said measured rotational movement being broken down into a rotation measured around the central axis of vision and at least one rotation measured around an axis perpendicular to the central axis of vision, the method moreover containing the steps of:
    modifying the at least one frame by applying a rotational movement to the intersecting plane corresponding to said frame, said rotational movement being contrary to the at least one rotation measured around the axis perpendicular to the central axis of vision,
    displacing the lines around the central axis of vision according to a rotational movement contrary to the rotation measured around the central axis of vision.

2. Method according to claim 1, in which the definition of at least one frame defines a plurality of frames corresponding to intersections of planes parallel to each other and in which the parallel planes are affected by the same rotational movement.

3. Method according to claim 1, in which the motion sensor contains three linear accelerometers making it possible to measure a direction of gravity and in which the measured rotational movement corresponds to the rotation of the direction of gravity with respect to a reference direction of gravity.

4. Method according to claim 1, in which, when the rotation measured around an axis perpendicular to the central axis of vision is greater than a critical angle ($\alpha_{crit}$), the intersecting plane or planes are replaced with new intersecting planes having been subjected to a rotation of twice the critical angle ($\alpha_{crit}$).

5. Method according to claim 1, in which the display of the three-dimensional image is effected with a colour and/or an intensity which varies over time.

6. Method according to claim 1, in which the display of the three-dimensional image is effected with a colour and/or an intensity which varies as a function of the position of each pixel in the three-dimensional image.

7. Method according to claim 1, in which the central axis of vision (130) corresponds to a direction of the user's gaze.

8. Method according to claim 1, in which the central axis of vision (130) points at an area of interest of the displayed image.

9. Method according to claim 1, in which the at least one motion sensor measures a translational movement according to the central axis of vision and in which the frame or frames are displaced translationally along the central axis of vision in a direction contrary to the direction of the measured translational movement.

10. Method according to claim 1, in which the at least one motion sensor measures a translational movement according to an axis perpendicular to the central axis of vision and in which the lines are displaced translationally in a direction contrary to the direction of the measured translational movement.

11. Visualization device containing at least one screen masking all or part of the field of vision of a user, and at least one motion sensor which is integral with the screen, wherein it contains a central processing unit capable of storing and executing computer programs, in which one of the programs, when it is executed, performs the method according to claim 1.

* * * * *